US005681608A

United States Patent [19]
Cain et al.

[11] Patent Number: 5,681,608
[45] Date of Patent: Oct. 28, 1997

[54] NUTRIENT FATS HAVING IMPROVED DIGESTIBILITY

[75] Inventors: Frederick William Cain, Voorburg, Netherlands; Paul Thomas Quinlan, Bedford, Great Britain

[73] Assignee: Loders Croklaan B.V., Wormerveer, Netherlands

[21] Appl. No.: 532,631

[22] PCT Filed: Mar. 31, 1994

[86] PCT No.: PCT/EP94/01041

§ 371 Date: Oct. 12, 1995

§ 102(e) Date: Oct. 12, 1995

[87] PCT Pub. No.: WO94/24889

PCT Pub. Date: Nov. 10, 1994

[30] Foreign Application Priority Data

Apr. 23, 1993 [EP] European Pat. Off. ............ 93303171

[51] Int. Cl.⁶ .................................................. A23D 9/00
[52] U.S. Cl. .................................... 426/606; 426/607
[58] Field of Search ............................ 426/607, 606

[56] References Cited

U.S. PATENT DOCUMENTS

| 4,996,074 | 2/1991 | Seiden | 426/607 |
|---|---|---|---|
| 5,137,660 | 8/1992 | Mazur et al. | 536/18.2 |
| 5,258,197 | 11/1993 | Wheeler | 426/607 |
| 5,288,512 | 2/1994 | Seiden | 426/607 |
| 5,366,752 | 11/1994 | Cain | 426/607 |
| 5,378,490 | 1/1995 | Wheeler | 426/607 |
| 5,380,544 | 1/1995 | Klemann | 426/607 |
| 5,407,695 | 4/1995 | Wheeler | 426/607 |
| 5,411,756 | 5/1995 | Wheeler | 426/607 |
| 5,456,939 | 10/1995 | Wheeler | 426/607 |
| 5,552,174 | 9/1996 | Wheeler | 426/607 |

FOREIGN PATENT DOCUMENTS

| 0 209 176 | 1/1987 | European Pat. Off. . |
|---|---|---|
| 0 271 909 | 6/1988 | European Pat. Off. . |
| 0 422 490 A2 | 4/1991 | European Pat. Off. . |
| WO 89/02275 | 3/1989 | WIPO . |
| WO 91/09597 | 7/1991 | WIPO . |
| WO 92/19237 | 11/1992 | WIPO . |

OTHER PUBLICATIONS

Kaimal et al, The Journal of the Oil Technologists' Association of India, 21(1):2–10 (1989).
Patent Abstracts of Japan, vol. 16, No. 269 (C–0952) Jun. 17, 1992 and JP A 04 066 052.
Derwent Publications, Ltd., London, AN 93-121655 and JP 5 059 392 (Mar. 9, 1993).

*Primary Examiner*—Carolyn Paden
*Attorney, Agent, or Firm*—Cushman Darby & Cushman IP Group Pillsbury Madison & Sutro LLP

[57] ABSTRACT

The invention concerns triglyceride compositions useful as nutrient fats having improved digestibility. The compositions comprise:

1–95 wt. % of $M_2L$;
5–65 wt. % of $ML_2$,
M=saturated fatty acid $C_2$–$C_{14}$;
L=unsaturated fatty acid $C_{18}$+,
35–99.5% of the total L being bonded at the 2-position.

14 Claims, No Drawings

NUTRIENT FATS HAVING IMPROVED DIGESTIBILITY

This application claims benefit of international application PCT/EP94/01041, filed Mar. 31, 1994.

BACKGROUND OF THE INVENTION

Synthetic triglycerides comprising two different groups of fatty acid residues, i.e. fatty acids consisting of ω-3 unsaturated fatty acids and saturated fatty acids in the $C_8$–$C_{10}$ range, wherein the fatty acid residues of the saturated $C_8$–$C_{10}$ range are preferably bonded to the 1,3-positions, while the ω-3 fatty acids are preferably derived from plant oils, marine plankton oils, fungal oils or fish oils are known from U.S. Pat. No. 4,873,768 (although this is contradictory to the disclosure in column 4, lines 7–10 of U.S. Pat. No. 4,873,768, where it is stated that the saturated $C_8$–$C_{10}$ fatty acid residues are preferably bonded to adjacent carbon atoms). A prerequisite for these triglycerides is that at least one ω-3 fatty acid residue is present and at least one $C_8$–$C_{10}$ saturated fatty acid residue. Therefore, the maximum amount of ω-3 fatty acid residues is 66 wt. % (i.e. two of these residues are present) from which at least 50% is bonded at the 2-position.

The above-mentioned triglycerides can be used in enterally or parenterally administered compositions. The above-mentioned fats provide a means for the addition of fat calories while the fats do not give rise to problems in the the reticulo-endothecial system and do not act as substrates for prostaglandin systems.

According to U.S. Pat. No. 4,906,664, nutritional supports for patients suffering from cancer cachexia are obtained when the diet contains an amount of triglycerides containing medium-chain fatty acids and unsaturated ω-3 long-chain fatty acid.

In WO 92/19237, pharmaceutical compositions are disclosed that can be used in enteral preparations for treatment of lipid malabsorption. The lipids contain MLM-type triglycerides (M=medium-chain fatty acids $C_6$–$C_{13}$ and L=long-chain fatty acids $C_{14}$–$C_{24}$, e.g. unsaturated fatty acid residues). It is disclosed that the lipid absorption is greater for MLM than for randomized MLM triglycerides.

According to WO 91/095597, triglycerides that contain at least one $C_2$–$C_5$ fatty acid residue and at least one $C_{16}$–$C_{24}$ fatty acid residue can be used as a biological agent with effect on the intestinal mucosa.

From the above-mentioned references it can therefore be concluded that fat absorption, and therefore the digestibility of a fat, is improved when the 1,3-positions in the fat are taken by medium-chain fatty acids. So, if a graph were to be drawn, demonstrating the digestibility against the content of medium-chain fatty acids in the 1,3-positions, it would be found that the digestibility of MLM fat (=M=medium-chain fatty acid) would be far better than that of LLL fats. Simultaneously, digestibility would be expected to be in linear relationship to the percentage of medium-chain fatty acids present in the 1,3-positions of triglycerides. Surprisingly, however, it was found that the digestibility of fats comprising a mixture of $M_2L$ and $L_2M$ fats with an overall M content in the 1,3-position varying between 0 and 100% has a digestibility which is greater than expected in theory.

SUMMARY OF THE INVENTION

Therefore, we found triglyceride compositions having a digestibility that is higher than should be expected. These triglyceride compositions comprise fats derived from saturated medium/short-chain fatty acids and fats derived from long-chain unsaturated fatty acids, wherein the composition comprises:

1–95 wt. % of $M_2L$-type triglycerides and

5–65 wt. % of $L_2M$-type triglycerides,

M being saturated fatty acid residues with 2–14 carbon atoms, preferably 6–14 carbon atoms;

L being mono- or poly-unsaturated fatty acid residues with at least 18 carbon atoms, the fatty acid distribution of L being such that 35–99.5%, preferably 40–80%, of the total L present being bonded at the 2-position.

DETAILED DESCRIPTION OF THE INVENTION

Although the above-mentioned triglycerides are all very useful, a preference is expressed for the use of fats wherein the total amount of L is not 33–67 wt. % in case L is $C_{18+\omega-3}$ only.

In particular, a preference is expressed for the application of a triglyceride composition according to the invention, wherein the amount of $M_2L$=10–50 wt. % and the amount of $L_2M$=30–60 wt. %.

Although M can range from 2–14 C-atoms, a preference is expressed for the use of saturated fatty acid residues having 8–12 C atoms.

As unsaturated fatty acid residue L, a great number of different unsaturated fatty acids can be applied. Examples thereof are oleic, linolenic, linolenic (both α and γ) and the essential fatty acids having at least 20 C-atoms, such, as DHA (=$C_{22:6\omega3}$), E.P.A. (=$C_{20:5\omega3}$), or arachidonic acid (=$C_{20:4\omega6}$).

Although the above-mentioned triglycerides could be used per se, a preference is expressed for the application of blends of the above-mentioned fats with other fats. In these blends the presence is preferred of a structuring fat which makes it easier to apply the fats in food products.

Therefore, in another embodiment of the invention, We found blends of triglycerides comprising at least a fat A and a structuring fat B, wherein fat A is a fat according to the invention which is present in 0.3–70 wt. %, preferably 5–45 wt % fat B is a fat containing saturated fatty acid residues with 12–24 carbon atoms, its SAFA content being 20–80 wt. %, which fat B is present in amounts of 30–99.7 wt. %, preferably 55–95 wt %

The structuring properties of fat B are best when fat B displays a solid fat content at 20° C. (NMR pulse) of more than 15, preferably more than 20.

Suitable fats B are obtained by blending fats C and D, wherein fat C has an ($L_2S+L_3$) level of more than 35 wt. %, preferably 35–85 wt % and fat D displays an $N_{20}$>30, L being as defined above, S being saturated fatty acid residues with 16–22 C atoms.

The preferred fats B which display the best structuring properties are fats B, wherein more than 25 wt %, preferably 25–60 wt % of $LS_2$ is present (L and S as defined above).

Other suitable fats B have an ($H_2M'+M'H_2$) content of more than 60 wt. %, H being saturated fatty acid residue with $\geq 16$ C-atoms, preferably 16–18 C-atoms, M' being saturated fatty acid residue with 8–14 C-atoms, preferably 12–14 C-atoms.

The blends very suitably should display SAFA levels of 20–40 wt. %, MUFA levels of 10–70 wt. % and PUFA levels of 10–70 wt. %, while simultaneously the ratio between ω-6 and ω-3 unsaturated fatty acids should vary from 2–20, preferably from 4–15.

The fats and fat blends according to the invention can be applied as a fat phase in food products, such as spreads, margarines, cream alternatives, chocolate, confectionery, bakery products, sauces, ice creams, table oils, dressings, mayonnaises, enteral or parenteral products, wherein the fat phase at least partly comprises a fat according to the invention. The fats are also very useful in infant formulas, in which case the compositions also comprise proteins and carbohydrates (cf. EP 496.456).

The amount of fat in these products can vary between wide ranges, suitable amounts being 1–80 wt. %; however, the actual amount will depend largely on the food product.

The fats according to our invention can be made by applying enzymic conversions, e.g. as disclosed in GB 1,577,933. The starting materials have to be selected carefully. Sources for the medium-chain fatty acids are, e.g., palm kernel oils or coconut oils. Sources for the unsaturated long-chain fatty acids are, e.g., sunflower oil, high-oleic sunflower oil, soybean oil, rapeseed oil, borage, evening primrose oil, fish oil, safflower oil, linseed or oils derived from algal or fungal sources, such as *Mortierella* species.

EXAMPLES

1. Preparation of an MLM-rich fat 1.1 Glycerol (1.25 g) was reacted with decanoic anhydride (8.86 g) in the presence of dichloromethane (63 ml) and Rhizomucor miehei lipase (2.5 g supported lipase). The reaction was performed for 10 hrs at 20° C. The product mixture was filtered and cooled over dry-ice. The precipitate (1.3-dicaprin) was collected and treated with silica to yield 2.76 g purified diglyceride.

1.2 The diglyceride was reacted with 3.75 g linoleic anhydride in the presence of 60 ml dichloromethane and 4-N,N-dimethylaminopyridine (0.255 g). After 2 hrs at 20° C., the mixture was cooled over dry-ice and the product collected by filtration (yield 7.6 g). After purification over alumina 4.8 g of a pure product was obtained. From analysis we could conclude that this product contained 99% $M_2L$, comprising 66.8 wt % $C_{10:0}$ and 33.2 wt % $C_{18:2}$, while 84.6% of the 1.3-positions were occupied by $C_{10:0}$ (on mole basis).

2. Digestibility

The digestibility of the above MLM-fat was measured as follows:

1 g of fat was added to 100 ml of an aqueous solution containing 0.261 g sodium taurodeoxycholate, 0.368 g calcium chloride and 0.877 g sodium chloride. An emulsion was formed by homogenisation and ultrasonication, and pH adjusted to 7.0. Hydrolysis of the emulsion was determined by addition of 20–40 μl of 1% solution of crude pancreatic lipase (Sigma Type II, buffered to 0 ml of the emulsion at 37°–40° C. Fatty acid released by the lipase was neutralised by addition of sodium hydroxide to maintain a pH of 7.0. Rate of hydrolysis was calculated from the rate of reagent added. Mean slope was determined by linear regression in the time interval from 2 to 10 minutes after addition of enzyme. We found a digestibility of 107.

3. The digestibility of sunflower oil SF-1 was measured by the same procedure (63% $C_{18:2}$; 24% $C_{18:1}$; % M in 1.3:0%). We found a digestibility of 100.

4. For comparison sunflower oil (SF-1) was reacted with $C_{10:0}$ fatty acid in the presence of Rhizomucor miehei lipase. At the end of the reaction the fatty acids and partial glycerides were removed, and the product (SF-2) characterised:

|  | FAME | 2-position |
|---|---|---|
| $C_{8:0}$ | 0.6 | 0.1 |
| $C_{10:0}$ | 27.3 | 0.9 |
| $C_{12:0}$ | 0.2 | — |
| $C_{14:0}$ | — | — |
| $C_{16:0}$ | 3.4 | 0.8 |
| $C_{18:0}$ | 3.2 | 3.1 |
| $C_{18:1}$ | 17.9 | 25.1 |
| $C_{18:2}$ | 46.5 | 68.3 |
| $C_{20}$ | 0.3 | 0.6 |
| $C_{22}$ | 0.6 | 0.1 |
| $C_{24}$ | 0.2 |  |

48% of the total 'L' ($C_{18:1}+C_{18:2}$) was esterified to the sn-2 position. The sn-1,3 positions comprised −54% $C_{8:0}+C_{10:0}$ on a mole basis.

The $M_2L$ content and $ML_2$ content of SF-2 was 41.0% and 38.9% respectively. The digestibility of the two oils was measured as described above with the following result:

|  | Relative lipolysis rate (mean ± SEM) |
|---|---|
| SF-1 | 100 ± 1.8 (n = 8) |
| SF-2 | 113.4 ± 2.7 (n = 8) |

The SF-2 oil was hydrolysed in vitro at a significantly faster rate compared to the SF-1 oil.

5. From the above, it can be concluded that the digestibility of SF-1 was 100 (so for 0% M in 1.3); for SF-2 we found 113.4 (for 54% $C_{10}+C_8$ in 1.3) and for MLM (with 84.6% M in 1.3) we found 107. So, the SF-2 showed a digestibility that is greater than could be expected on basis of a linear relationship between % M in 1.3 and the digestibility.

We claim:

1. Triglyceride composition comprising fats derived from saturated medium/short-chain fatty acids and fats derived from long-chain unsaturated fatty acids, wherein the composition comprises:

1–95 wt. % of $M_2L$-type triglycerides and

5–65 wt. % of $L_2M$-type triglycerides,

M being saturated fatty acid residues with 2–14 carbon atoms,

L being mono- or poly-unsaturated fatty acid residues with at least 18 carbon atoms, the fatty acid distribution of L being such that 35–99.5%, of the total L present being bonded at the 2-position.

2. Triglyceride composition according to claim 1, wherein the amount of $M_2L$=10–50 wt. % and the amount of $L_2M$= 30–60 wt. %.

3. Triglyceride composition according to claim 1, wherein

M is saturated $C_8$–$C_{12}$ fatty acid residue and

L is mono- or poly-unsaturated $C_{18}$ fatty acid residue from oleic acid, linoleic acid or linolenic acid.

4. Triglyceride composition according to claim 1, wherein L is an essential fatty acid with at least 20 carbon atoms.

5. Triglyceride composition according to claim 4 wherein is DHA ($C_{22:\omega3}$) or E.P.A. ($C_{20:5\omega3}$).

6. Blend of triglycerides comprising at least a fat A and a structuring fat B, wherein fat A is a fat according to claim 1 and is present in 0.3–70 wt. %;

fat B is a fat containing saturated fatty acid residues with 12–24 carbon atoms, its SAFA content being 20–80 wt. %, which fat B is present in amounts of 30–99.7 wt. %.

7. Blend according to claim 6, wherein fat B displays a solid fat content at 20° C. (NMR pulse) of more than 20.

8. Blend according to claim 6, wherein fat B displays a solid fat content at 20° C. (NMR pulse) of more than 15.

9. Blend according to claim 6, wherein fat B is obtained by blending fats C and D, wherein fat C has an ($L_2S+L_3$) level of more than 35 wt. % and fat D displays an $N_{20}>30$, L being as defined in claim 1, S being saturated fatty acid residues with 16–22 C atoms.

10. Blend according to claim 9, wherein fat B has an $LS_2$ content of more than 25 wt. %.

11. Blend according to claim 6, wherein fat B has an ($H_2M'+M'_2H$) content of more than 60 wt %, H being saturated fatty aid residue with $\geq 16$ C-atoms, M' being saturated fatty acid residue with 8–14 C-atoms and wherein L is oleic, linolenic, DHA ($C_{22:\omega 3}$), E.P.A. ($C_{20:5\omega 3}$) or arachidonic acid ($C_{20:4w6}$).

12. Blend according to claim 11 wherein H is a saturated fatty acid residue with 16–18 C-atoms and M' is a saturated fatty acid residue with 12–14 C-atoms.

13. Food products comprising at least a fat phase, such as spreads, margarines, cream alternatives, chocolate, confectionery, bakery products, sauces, ice creams, table oils, dressings, mayonnaises, enteral or parenteral products wherein the fat phase at least partly comprises a fat according to claim 1.

14. Triglyceride composition according to claim 1 wherein M is a saturated fatty acid residue with 6–14 carbon atoms and the fatty acid distribution of L is 40–80%.

* * * * *